(12) United States Patent
Yamamoto

(10) Patent No.: US 7,521,472 B2
(45) Date of Patent: Apr. 21, 2009

(54) CRYSTAL OF TWO-RING HETEROCYCLIC SULFONAMIDE COMPOUND

(75) Inventor: Eiichi Yamamoto, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 11/667,150

(22) PCT Filed: Nov. 8, 2005

(86) PCT No.: PCT/JP2005/020414

§ 371 (c)(1),
(2), (4) Date: May 7, 2007

(87) PCT Pub. No.: WO2006/054456

PCT Pub. Date: May 26, 2006

(65) Prior Publication Data

US 2007/0299266 A1     Dec. 27, 2007

(30) Foreign Application Priority Data

Nov. 17, 2004   (JP) ............................. 2004-332855

(51) Int. Cl.
*A61K 31/404* (2006.01)
*C07D 209/04* (2006.01)
(52) U.S. Cl. ...................... 514/415; 548/469
(58) Field of Classification Search ................. 548/507, 548/469, 490, 491; 514/415
See application file for complete search history.

(56) References Cited

U.S. PATENT DOCUMENTS 5,721,246 A * 2/1998 Yoshino et al. ............. 514/300

FOREIGN PATENT DOCUMENTS

| JP | 9-316053 A | 12/1997 |
|---|---|---|
| WO | WO-95/07276 A1 | 3/1995 |
| WO | WO-03/022271 A1 | 3/2003 |
| WO | WO-03/022272 A1 | 3/2003 |

OTHER PUBLICATIONS

Golub et al., Molecular Classification of Cancer: Class Discovery and Class Prediction by Gene Expression Monitoring, Oct. 15, 1999, Science, vol. 286, p. 531.*
Peeyush K. Lala and Amila Orucevic, Role of nitric oxide in tumor progression: Lessions from experimental tumors, 1998, Cancer and Metastasis Reviews, vol. 17, p. 91.*
Owa et al., Discovery of Novol Antitumor Sulfonamides Targeting G1 Phase of the Cell Cycle, Journal of Medicinal Chemistry, 1999, vol. 42, No. 19, pp. 3789-3799.

* cited by examiner

*Primary Examiner*—Kamal A Saeed
*Assistant Examiner*—Kristin Bianchi
(74) *Attorney, Agent, or Firm*—Birch, Stewart, Kolasch & Birch, LLP

(57) ABSTRACT

Novel β-type crystal of N-(3-chloro-1H-indol-7-yl)-4-sulfamoylbenzenesulfonamide of the formula: characterized in, for example, that in powder X-ray diffractometry, it has a diffraction peak at a diffraction angle (2θ±0.2°) of 18.4°. This crystal has favorable properties, such as high solubility in buffer solutions and various organic solvents, and is suitable to an active ingredient of a pharmaceutical composition for use as an antitumor agent, an activated lymphocyte suppressor or an eating enhancer.

6 Claims, 1 Drawing Sheet

CRYSTAL OF TWO-RING HETEROCYCLIC SULFONAMIDE COMPOUND

TECHNICAL FIELD

The present invention relates to a crystal of N-(3-chloro-1H-indol-7-yl)-4-sulfamoylbenzenesulfonamide, a bicyclic heterocycle-containing sulfonamide compound having antitumor activity, and use thereof.

BACKGROUND ART

Bicyclic heterocycle-containing sulfonamide compounds are useful as antitumor agents, and among them, N-(3-chloro-1H-indol-7-yl)-4-sulfamoylbenzenesulfonamide (hereafter sometimes abbreviated as Compound (1)) exhibits remarkable antitumor activity (see Patent Document 1), activated lymphocyte suppressive action (see Patent Document 2), or eating enhancement action (see Patent Document 3).

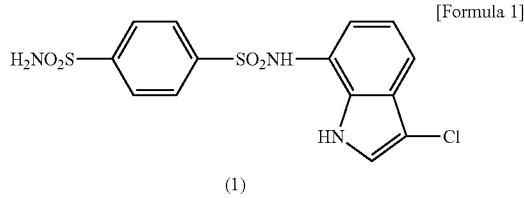

[Formula 1]

(1)

The compound (1) is a known compound, and a production method thereof is disclosed in Example 19 of Patent Document 1. The document describes " . . . to give 349 mg of the title compound. . . . (recrystallized from ethanol-n-hexane)". It discloses only a melting point and a nuclear magnetic resonance spectrum thereof as physical properties of the crystal, but does not disclose or suggest the existence of crystal polymorphs other than the above description of crystal.

Patent Document 1: International Publication WO 95/07276 pamphlet
Patent Document 2: International Publication WO 03/022271 pamphlet
Patent Document 3: International Publication WO 03/022272 pamphlet

DISCLOSURE OF THE INVENTION

Problems to be Solved by the Invention

The physical properties of a drug substance crystal for a pharmaceutical product greatly affect the bioavailability of a drug, the purity of the drug substance, pharmaceutical formulation, and the like. Therefore, the development of pharmaceutical products requires studies on which crystal polymorph is the most excellent as a pharmaceutical product among crystal polymorphs that can be crystallized by production methods.

Accordingly, it is the object of the present invention to provide a crystal that is different in polymorphism from the crystal of the compound (1) described in International Publication WO 95/07276 pamphlet and is more suitable for pharmaceutical formulation.

Means for Solving the Problems

Since the physical properties of a drug substance crystal for a pharmaceutical product greatly affect the bioavailability of a drug, the purity of the drug substance, pharmaceutical formulation, and the like, the crystal polymorphism of a drug substance and its physical properties are important factors for the development of pharmaceuticals.

Therefore, the present inventor has made various studies to elucidate crystal forms available as crystal polymorph of the compound (1). As a result, the inventor has studied recrystallization conditions other than those for the crystal (hereafter indicated as α-type crystal) described in Patent Document 1, and thereby found a novel crystal (hereafter indicated as β-type crystal) according to the present application, completing the present invention.

Specifically, the present invention relates to a crystal of N-(3-chloro-1H-indol-7-yl)-4-sulfamoylbenzenesulfonamide having a diffraction peak at a diffraction angle (2θ±0.2°) of 18.4° by powder X-ray diffractometry.

Preferably, the present invention relates to the crystal of N-(3-chloro-1H-indol-7-yl)-4-sulfamoylbenzenesulfonamide further having a diffraction peak at a diffraction angle (2θ±0.2°) of 10.2° by powder X-ray diffractometry.

Preferably, the present invention relates to the crystal of N-(3-chloro-1H-indol-7-yl)-4-sulfamoylbenzenesulfonamide further having a diffraction peak at a diffraction angle (2θ±0.2°) of 15.4° by powder X-ray diffractometry.

Preferably, the present invention relates to the crystal of N-(3-chloro-1H-indol-7-yl)-4-sulfamoylbenzenesulfonamide further having a diffraction peak at a diffraction angle (2θ±0.2°) of 13.3° by powder X-ray diffractometry.

Preferably, the present invention relates to the crystal of N-(3-chloro-1H-indol-7-yl)-4-sulfamoylbenzenesulfonamide further having a diffraction peak at a diffraction angle (2θ±0.2°) of 20.4° by powder X-ray diffractometry.

Preferably, the present invention relates to the crystal of N-(3-chloro-1H-indol-7-yl)-4-sulfamoylbenzenesulfonamide further having a diffraction peak at a diffraction angle (2θ±0.2°) of 20.0° by powder X-ray diffractometry.

Further, the present invention relates to a pharmaceutical composition containing any of the above-described crystals as an active ingredient. Preferably, the present invention relates to a pharmaceutical composition for antitumor activity, activated lymphocyte suppression, or eating enhancement.

Effects of the Invention

The present invention enables the obtainment of a novel crystal (β-type crystal) as a single crystal form by using, for example, acetonitrile-water (1:1) or isopropanol-water (1:1) as a recrystallization solvent by solvent evaporation method. The thus-obtained novel crystal is different from the crystal (α-type crystal) obtained by the production method described in Example 19 of Patent Document 1 (International Publication WO 95/07276 pamphlet). The crystal of the present invention has good physical properties such as high solubility in buffer solutions (for example, Britton-Robinson Buffer) and various organic solvents (for example, ethanol, ethyl acetate) in comparison with α-type crystal, and is suitable for an active ingredient of a pharmaceutical composition used as an antitumor agent, an activated lymphocyte suppressor, or an eating enhancer.

Figure 1:
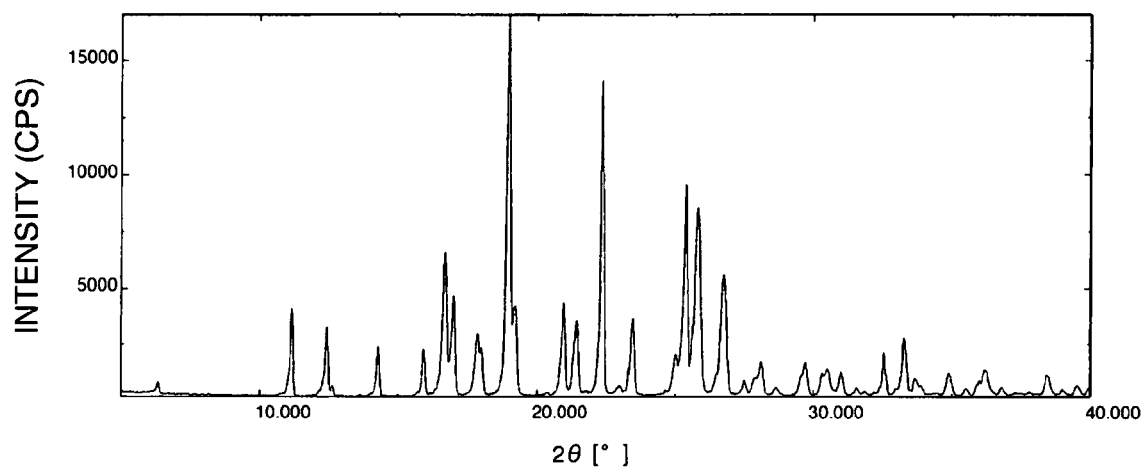
FIG. 1 shows a powder X-ray diffraction pattern of α-type crystal, the compound (1) obtained in Reference Example 4. The abscissa and ordinate thereof indicate a diffraction angle (2θ) and a peak strength, respectively.

Next, a β-type crystal of the present invention and its production method are described in detail.

The crystal of the present invention is a crystal of the compound (1), and featured by having diffraction peaks at, for example,
(1) 18.4°;
(2) 10.2°;
(3) 15.4°;
(4) 13.3°;
(5) 20.4°; and
(6) 20.0°.

The characteristic peaks of these powder X-ray diffractions are specific to the β-type crystal, and they are not observed in the α-type crystal.

Since the diffraction angle (2θ) by powder X-ray diffractometry generally has an error in the range of ±0.2°, the above-mentioned values for the diffraction angle must be interpreted as including values within a range of about ±0.2°. Thus, the present invention encompasses not only crystals that have peak diffraction angles by powder X-ray diffractometry exactly matching the above, but also crystals that are considered matching though having an error of peak diffraction angles in the range of about ±0.2°.

In the present specification, "having a diffraction peak at a diffraction angle (2θ+0.2°) of 18.4°" means "having a diffraction peak at a diffraction angle (2θ) in the range of 18.2° to 18.6°"; "having a diffraction peak at a diffraction angle (2θ+0.2°) of 10.2°" means "having a diffraction peak at a diffraction angle (2θ) in the range of 10.0° to 10.40"; "having a diffraction peak at a diffraction angle (2θ+0.2°) of 15.4°" means "having a diffraction peak at a diffraction angle (2θ) in the range of 15.2° to 15.6°"; "having a diffraction peak at a diffraction angle (2θ+0.2°) of 13.3°" means "having a diffraction peak at a diffraction angle (2θ) in the range of 13.1° to 13.5°"; "having a diffraction peak at a diffraction angle (2θ+0.2°) of 20.4°" means "having a diffraction peak at a diffraction angle (2θ) in the range of 20.2° to 20.6°"; and "having a diffraction peak at a diffraction angle (2θ+0.2°) of 20.0°" means "having a diffraction peak at a diffraction angle (2θ) in the range of 19.8° to 20.2°".

Crystallization Method of β-Type Crystal Using Various Recrystallization Solvents The β-type crystal of the present invention is produced by producing the compound (1) in accordance with Example 19 of the above Patent Document 1 (International Publication No. 95/07276 pamphlet), dissolving the obtained compound (1) (α-type crystal) in a predetermined solvent, and allowing the solution to stand at room temperature to produce the crystal.

The compound (1) used for crystallization has good crystallinity. Thus, under the conditions of the foregoing Example 19, the compound can usually be obtained in the form of α-type crystal, but any form may be acceptable, for instance, hydrated or anhydrous, amorphous or crystalline (including more than one crystal polymorph), or in combination therefrom.

The solvent to be used for crystallization may be a single solvent or a mixed solvent of two or more selected from the group consisting of alkylketone solvents such as acetone; acetonitrile; alcohol solvents such as ethanol and isopropanol; and water. Preferred is a single solvent or a mixed solvent of two or more selected from the group consisting of, for example, acetonitrile, isopropanol, and water. Particularly, acetonitrile-water and isopropanol-water, for example, are preferred.

When the mixed solvent of acetonitrile-water or isopropanol-water is used, the mixing ratio (volume ratio) thereof is preferably 5:1 to 1:5, more preferably 3:1 to 1:3, and still more preferably 2:1 to 1:2. The most preferable is solvent evaporation method using a mixed solvent of acetonitrile-water (1:1) or isopropanol-water (1:1). Further, vapor diffusion method using acetonitrile or isopropanol may be employed.

The amount of the solvent to be used may properly be selected in the range from the minimum amount that dissolves the compound (1) by heating to the maximum amount that does not significantly reduce the yield of the crystals. Preferably, the volume ratio of the solvent to the weight of the compound (1) is, for example, 5 to 50 fold amount (v/w). As the amount of recrystallization solvent, the ratio is preferably, for example, 5 to 30 fold amount (v/w), more preferably about 10 fold amount (v/w) when acetonitrile-water (1:1) is used as recrystallization solvent, and about 10 fold amount (v/w) when isopropanol-water (1:1) is used as recrystallization solvent.

The heating temperature for dissolution of the compound (1) may appropriately be selected depending on the solvent, but it is preferably, for example, from the reflux temperature of the recrystallization solvent to 15° C., more preferably, for example, 35° C. to 15° C.

Since variations of cooling rate during crystallization afford crystals having different forms (polymorphism), it is desired to carry out the cooling while properly adjusting the cooling rate in consideration of the effect on quality, particle size, and the like of the crystals. The cooling rate is preferably, for example, 40° C. to 5° C. per hour, more preferably 25° C. to 15° C. per hour.

The final crystallization temperature may properly be selected depending on the yield, quality, and the like of the crystals, but preferably, for example, 10° C. to −25° C.

For crystallization, it does not matter whether a seed crystal (a small amount of β-type crystal of N-(3-chloro-1H-indol-7-yl)-4-sulfamoylbenzenesulfonamide) is added or not. The temperature for addition of the seed crystal is not particularly limited, but preferably 60° C. or lower for example, more preferably 55° C. to 0° C. for example, still more preferably 55° C. to 15° C. for example, and the most preferably about 25° C.

The precipitated crystals may be separated by an ordinary filtration procedure, washed with an appropriate solvent if necessary, and then dried to afford the crystals of interest. The solvent to be used for washing the crystals is generally the same as the crystallization solvent, and it is preferably a mixed solvent of acetonitrile-water (1:1) or a mixed solvent of isopropanol-water (1:1).

Method for Drying Crystals

The crystals separated by the filtration procedure can be dried by allowing them to stand in air or heating them, if appropriate.

The time period for drying until the residual solvent amount becomes lower than the predetermined one may properly be selected depending on the production amount, drying apparatus, drying temperature, and the like. Further, the drying may be carried out under airflow or under reduced pressure. The degree of reduced pressure may properly be selected depending on the production amount, drying apparatus, drying temperature, and the like. The obtained crystals, after being dried, may be allowed to stand in air if necessary.

The β-type crystal obtained by the above method has a single crystal form, and its crystal form is stable and thus not easily transformed into other crystal forms or amorphous forms. Further, the crystal has good physical properties such as non hygroscopicity, and is suitable for formulation.

The use of the compound (1) as an antitumor agent is disclosed in detail in Patent Document 1; the use of the compound (1) as an activated lymphocyte suppressor and a therapeutic agent for autoimmune diseases is disclosed in detail in Patent Document 2; and the use of the compound (1)

as an eating enhancer and a therapeutic agent for anorexia is disclosed in detail in Patent Document 3, and all of them exhibit good results. The β-type crystal of the present invention can be used in the same manner as an active ingredient of, for example, therapeutic agents for various tumors, an activated lymphocyte suppressor, a therapeutic agent for autoimmune diseases, an eating enhancer or a therapeutic agent for anorexia.

When the compound (1) of the present invention is used as a drug, it is orally or parenterally administered, for example, as an antitumor agent, an activated lymphocyte suppressor, a therapeutic agent for autoimmune diseases, an eating enhancer, or a therapeutic agent for anorexia. The dose thereof varies depending upon the extent of symptom; the age, sex, weight and sensitivity of a patient; the method, timing and interval of administration; the properties, dispensing and type of pharmaceutical preparation; the type of an active ingredient and the like, but it is not particularly limited. The dose per adult a day is 10 to 6000 mg, preferably about 50 to 4000 mg, more preferably about 100 to 3000 mg, which is generally divided into 1 to 3 portions for daily administration.

A solid preparation for oral administration is prepared by adding an excipient and, if necessary, a binder, disintegrator, lubricant, colorant, corrigent, and the like to a base component, and forming the resulting mixture into a tablet, coated tablet, granule, fine granule, powder, capsule, or the like by a conventional method. As examples of the excipient, usable are lactose, corn starch, sucrose, glucose, sorbitol, crystalline cellulose and silicon dioxide; as examples of the binder, polyvinyl alcohol, ethylcellulose, methylcellulose, gum Arabic, hydroxypropylcellulose and hydroxypropylmethylcellulose; as examples of the lubricant, magnesium stearate, talc and silica; as examples of the colorant, those approved for addition to pharmaceutical products; and as examples of the corrigent, cocoa powder, menthol, aromatic acid, mentha oil, borneol and powdered cinnamon bark. As a matter of course, the tablet and granule may be suitably coated with sugar, gelatin or the like, if necessary. An injection is prepared by optionally adding, for example, a pH regulator, a buffer, a suspending agent, a solubilizing agent, a stabilizer, an isotonizing agent and a preservative to the base component and forming the obtained mixture into an injection for intravenous, subcutaneous or intramuscular administration by a conventional method. If necessary, the prepared injection may be freeze-dried by a conventional process. Examples of the suspending agent include methylcellulose, Polysorbate 80, hydroxyethylcellulose, gum Arabic, tragacanth powder, sodium carboxymethylcellulose and polyoxyethylene sorbitan monolaurate.

BEST MODE FOR CARRYING OUT THE INVENTION

Hereafter, the present invention is described in detail by referring to Reference Examples, Examples, and Test Examples, but not limited thereto.

REFERENCE EXAMPLE 1

Production of N-(3-chloro-1H-indol-7-yl)-4-sulfamoylbenzenesulfonamide (α-type crystal)

(1) 4-sulfamoylbenzenesulfonyl chloride

[Formula 2]

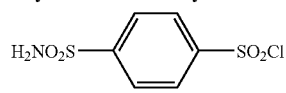

6.4 g (37.2 mmol) of 4-aminobenzenesulfonamide was added to a mixed solution of 12.5 ml of water and 6.3 ml of concentrated hydrochloric acid and stirred together. A saturated aqueous solution of 2.56 g (37.1 mmol) of sodium nitrite was added dropwise thereinto at 0° C. or lower. The reaction solution was added to an acetic acid solution saturated with sulfur dioxide (prepared by saturating sulfur dioxide in 35 ml of an acetic acid solution and adding 1.5 g of anhydrous cupric chloride to the saturated solution) while ice-cooled under stirring. After 10 minutes, the reaction solution was poured into iced water, and the resultant precipitates were collected by filtration and washed with water. The precipitates were dissolved in tetrahydrofuran, dried over magnesium sulfate, and concentrated to dryness to give 3.5 g of the title compound.

(2) 7-bromo-1H-indole

[Formula 3]

1.0M vinylmagnesium bromide in tetrahydrofuran 100 ml (100 mmol) was added to 250 ml of a solution of 5.05 g (25 mmol) of 2-bromonitrobenzene in tetrahydrofuran at −40° C. in a nitrogen atmosphere. The resultant mixture was stirred for 40 minutes. The reaction mixture was poured into 500 ml of a saturated aqueous solution of ammonium chloride. The mixture was extracted with ethyl ether. The extract was dried over magnesium sulfate and concentrated. The residue was purified by silica gel column chromatography to give 2.89 g of the title compound.

1H-NMR (DMSO-d6) δ (ppm): 6.56 (1H, dd, J=2.9, 1.8 Hz), 6.94 (1H, t, J=7.8 Hz), 7.30 (1H, d, J=7.8 Hz), 7.40 (1H, t, J=2.9 Hz), 7.56 (1H, d, J=7.8 Hz), 11.16-11.46 (1H, brm)

(3) 7-amino-1H-indole

[Formula 4]

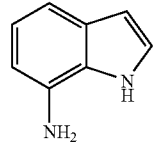

2.5M n-butyllithium in hexane 16.5 ml (41.3 mmol) was dropped into 50 ml of a solution of 2.70 g (13.8 mmol) of the above compound (2) in tetrahydrofuran at −70° C. in a nitrogen atmosphere. The mixture was stirred at −70° C. for 15 minutes and then at −20° C. to −10° C. for 30 minutes. The mixture was cooled to −70° C. again, followed by the dropwise addition of 3.9 ml (18 mmol) of diphenylphosphoryl azide. The resulting mixture was stirred at −70° C. for 1 hour and at −40° C. for 1 hour. 3.4M sodium bis(2-methoxyethoxy)aluminum hydride in toluene 22.3 ml (75.8 mmol) was added to the mixture at −40° C. The obtained mixture was stirred at −30° C. to −20° C. for 30 minutes and then at room temperature for 30 minutes, followed by the addition of a phosphate buffer of pH 7.0. The resulting mixture was filtered to remove insolubles and the filtrate was extracted with ethyl ether. An organic layer was washed with aqueous saturated sodium bicarbonate and aqueous saturated sodium chloride successively, dried over magnesium sulfate and concentrated. The residue was purified by silica gel column chromatography to give 1.29 g of the title compound.

1H-NMR (DMSO-d6) .δ (ppm): 5.01 (2H, br s), 6.25-6.33 (2H, m), 6.70 (1H, dd, J=7.9, 7.3 Hz), 6.78 (1H, dd, J=7.9, 0.7 Hz), 7.23 (1H, t, J=2.7 Hz), 10.48-10.72 (1H, brm)

(4) N-(3-chloro-1H-indol-7-yl)-4-sulfamoylbenzenesulfonamide (α-type crystal)

[Formula 5]

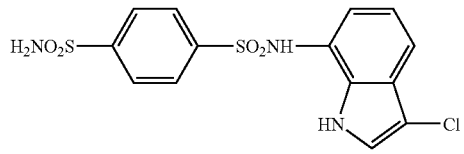

860 mg (6.5 mmol) of 7-amino-1H-indole obtained in the above (3) was dissolved in 5 ml of tetrahydrofuran, 5 ml of pyridine was added to the solution, and the mixture was ice cooled. After the mixture was stirred at 0° C. for 10 minutes, 1.83 g of 4-sulfamoylbenzenesulfonyl chloride (7.16 mmol) obtained in Reference Example 2 was added thereto and the resultant mixture was stirred at room temperature. After addition of ethyl acetate and 1N hydrochloric acid, the organic layer was separated and washed with aqueous saturated sodium bicarbonate and aqueous saturated sodium chloride successively. The organic layer was dried over magnesium sulfate, and the solvent was distilled under reduced pressure. The residue was purified by silica column chromatography (hexane/ethyl acetate=1.5/1 to 1/1) to give 1.812 g of N-(1H-indol-7-yl)-4-sulfamoylbenzenesulfonamide.

1.812 g (5.17 mmol) of this compound was dissolved in a mixed solvent of 150 ml of dichloromethane and 12 ml of dimethylformamide, and then 718 mg (5.27 mmol) of N-chlorosuccinimide was added to the solution while being stirred in a nitrogen atmosphere. After stirring at room temperature for 1 hour, an aqueous sodium thiosulfate solution and ethyl acetate were added thereto. The organic layer was separated and washed with aqueous saturated sodium bicarbonate and aqueous saturated sodium chloride successively. The organic layer was dried over magnesium sulfate and the solvent was distilled under reduced pressure. The residue was purified by silica gel column chromatography (hexane/ethyl acetate=1/1 to 2/1) to give 1.926 g of the title compound. The compound began to be discolored partially black around the melting point of 220° C., and was gradually decomposed around 240° C. (recrystallized from ethanol-n-hexane).

1H-NMR (DMSO-d6) .δ (ppm): 6.75 (1H, d, J=7.6 Hz), 6.96 (1H, dd, J=8.0, 7.6 Hz), 7.29 (1H, d, J=7.6 Hz), 7.50 (1H, d, J=2.8 Hz), 7.58 (2H, s), 7.90-7.98 (4H, m), 10.23 (1H, s), 11.07-11.17 (1H, m)

Powder X-Ray Crystal Diffraction of α-Type Crystal

A sample of the crystal (α-type crystal) obtained by the above crystallization method was pulverized using an agate mortar, placed on a sample table of a powder X-ray diffractometer, and analyzed under the following conditions.

The obtained powder X-ray diffraction pattern is shown in FIG. 1.

TABLE 1

| Measurement conditions | |
| --- | --- |
| Sample holder | Glass or Copper |
| Target | Copper |
| Detector | Scintillation counter |
| Tube voltage | 40 KV |
| Tube current | 200 mA |
| Slit | DSI/2°, RS 0.3 mm, SSI/2° |
| Scanning rate | 2°/min |

TABLE 1-continued

| Measurement conditions | |
| --- | --- |
| Sampling interval | 0.02° |
| Scanning range | 5 to 40° |
| Goniometer | Vertical goniometer |

EXAMPLE 1

N-(3-chloro-1H-indol-7-yl)-4-sulfamoylbenzenesulfonamide (β-type crystal)

[Formula 6]

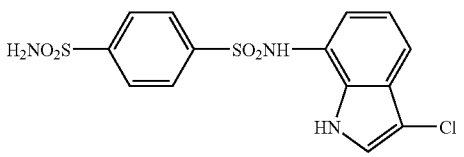

860 mg (6.5 mmol) of 7-amino-1H-indole obtained in (3) of Reference Example 1 was dissolved in 5 ml of tetrahydrofuran, 5 ml of pyridine was added to the reaction solution, and the reaction solution was ice cooled. After the reaction solution was stirred at 0° C. for 10 minutes, 1.83 g of 4-sulfamoylbenzenesulfonyl chloride (7.16 mmol) obtained in Reference Example 2 was added to the reaction solution and the resultant mixture was stirred at room temperature. After addition of ethyl acetate and 1N hydrochloric acid to the reaction solution, the organic layer was separated and washed with aqueous saturated sodium bicarbonate and aqueous saturated sodium chloride successively. The organic layer was dried over magnesium sulfate, and the solvent was distilled under reduced pressure. The obtained residue was purified by silica column chromatography (hexane/ethyl acetate=1.5/1 to 1/1) to give 1.812 g of N-(1H-indol-7-yl)-4-sulfamoylbenzenesulfonamide.

1.812 g (5.17 mmol) of this compound was dissolved in a mixed solvent of 150 ml of dichloromethane and 12 ml of dimethylformamide, and then 718 mg (5.27 mmol) of N-chlorosuccinimide was added to the solution while being stirred in a nitrogen atmosphere. After stirring at room temperature for 1 hour, an aqueous sodium thiosulfate solution and ethyl acetate were added thereto. The organic layer was separated and washed with aqueous saturated sodium bicarbonate and aqueous saturated sodium chloride successively. The organic layer was dried over magnesium sulfate and the solvent was distilled under reduced pressure. The residue was purified by silica gel column chromatography (hexane/ethyl acetate=1/1 to 2/1) to give 1.926 g of the title compound.

99.91 mg of N-(3-chloro-1H-indol-7-yl)-4-sulfamoylbenzenesulfonamide was dissolved in 100 ml of a mixed solvent of isopropanol-water (1:1) and the solvent was evaporated at room temperature at ordinary pressure in the dark to give β-type crystal (49.12 mg).

1H-NMR (DMSO-d6) .δ (ppm): 6.75 (1H, d, J=7.6 Hz), 6.96 (1H, dd, J=8.0, 7.6 Hz), 7.29 (1H, d, J=7.6 Hz), 7.50 (1H, d, J=2.8 Hz), 7.58 (2H, s), 7.90-7.98 (4H, m), 10.23 (1H, s), 11.07-11.17 (1H, m)

Powder X-ray Crystal Diffraction of β-Type Crystal

A sample of the crystal (β-type crystal) obtained by the above crystallization method was pulverized using an agate mortar, placed on a sample table of a powder X-ray diffractometer, and analyzed under the conditions of the following Table 2.

Figure 2:
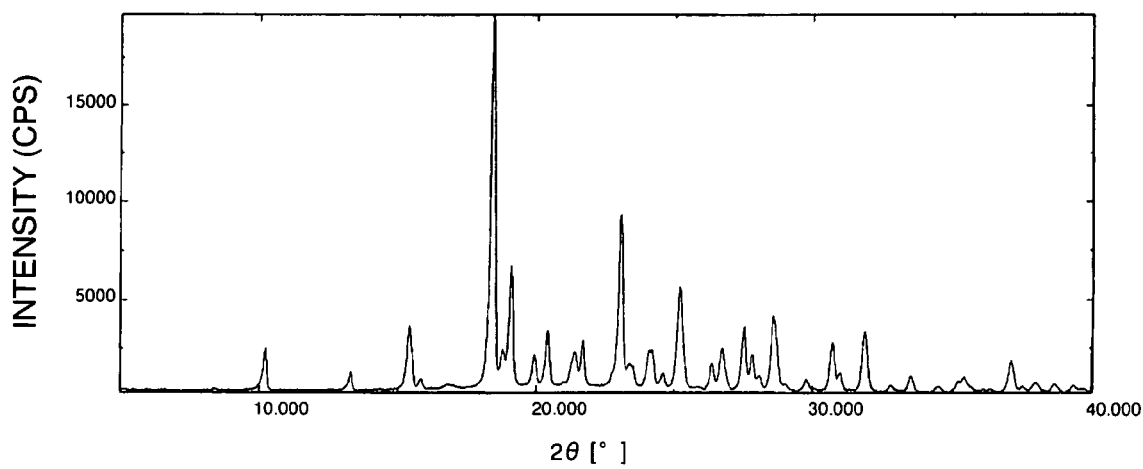
FIG. 2 shows a powder X-ray diffraction pattern of β-type crystal, the compound (1) obtained in Example 1. The abscissa and ordinate thereof indicate a diffraction angle (2θ) and a peak strength, respectively.

The obtained powder X-ray diffraction pattern is shown in FIG. 2.

TABLE 2

Measurement conditions

| Sample holder | Glass or Copper |
|---|---|
| Target | Copper |
| Detector | Scintillation counter |
| Tube voltage | 40 KV |
| Tube current | 200 mA |
| Slit | DSI/2°, RS 0.3 mm, SSI/2° |
| Scanning rate | 2°/min |
| Sampling interval | 0.02° |
| Scanning range | 5 to 40° |
| Goniometer | Vertical goniometer |

From the powder X-ray diffraction pattern of FIG. 2, it is observed that the β-type crystal characteristically has diffraction peaks at 18.4°, 10.2°, 15.4°, 13.3°, 20.4°, and 20.0°, for example, by powder X-ray diffractometry [diffraction angle (2θ)].

EXAMPLE 2

Crystallization of α-Type and β-Type Crystals Using Various Recrystallization Solvents Next, recrystallization was attempted using various recrystallization solvents by the solvent evaporation method and the temperature gradient method. The results thereof are shown in Tables 3 and 4.

1. Solvent Evaporation Method (1) Experiment method:

Approximately 100 mg of N-(3-chloro-1H-indol-7-yl)-4-sulfamoylbenzenesulfonamide was weighed in a beaker, and each of various solvents described in Table 3 was added until the compound was dissolved at 25° C. The beaker was covered with a perforated aluminum foil and placed under vacuum. The solvent was distilled at 25° C. in the dark, and the isolated crystals were collected and analyzed by powder X-ray diffractometry.

(2) Results:

According to the solvent evaporation method, the α-type crystal was selectively produced when the recrystallization solvent used was, for example, acetone, acetonitrile, isopropanol, acetone-water (1:1), methanol-water (1:1), or ethanol-water (1:1), and the β-type crystal was selectively produced when acetonitrile-water (1:1) or isopropanol-water (1:1) was used as an example.

TABLE 3

Recrystallization by solvent evaporation method

| Solvent | Crystal form |
|---|---|
| Acetone | α |
| Acetonitrile | α |
| Isopropanol | α |
| Methanol | α + β |
| Ethanol | α + β |
| Acetone-water (1:1) | α |
| Acetonitrile-water (1:1) | β |
| Isopropanol-water (1:1) | β |
| Methanol-water (1:1) | α |
| Ethanol-water (1:1) | α |

2. Temperature Gradient Method (1) Experiment method:

Approximately 100 mg of N-(3-chloro-1H-indol-7-yl)-4-sulfamoylbenzenesulfonamide was weighed in a round-bottom flask, melted once under a heating condition, and left at room temperature. The deposited crystals were collected by filtration, dried at 50° C., and analyzed by powder X-ray diffractometry. Various solvents described in Table 4 were used as the solvent. The temperature of the oil bath was 84.9° C. for acetone, 93.5° C. for acetone-water (1:1), and 100° C. for other solvents.

(2) Results:

According to the temperature gradient method, as shown in Table 4, the α-type crystal was selectively produced when the recrystallization solvent used was, for example, acetone, acetonitrile, isopropanol, methanol, ethanol, acetone-water (1:1), acetonitrile-water (1:1), isopropanol-water (1:1), methanol-water (1:1), or ethanol-water (1:1).

TABLE 4

Table 2.
Recrystallization by temperature gradient method

| Solvent | Crystal form |
|---|---|
| Acetone | α |
| Acetonitrile | α |
| Isopropanol | α |
| Methanol | α |
| Ethanol | α |
| Acetone-water (1:1) | α |
| Acetonitrile-water (1:1) | α |
| Isopropanol-water (1:1) | α |
| Methanol-water (1:1) | α |
| Ethanol-water (1:1) | α |

TEST EXAMPLE 1

Solubility of α-Type and β-Type Crystals in Organic Solvents and Buffer Solutions Next, in order to exhibit the usefulness of the β-type crystal of the present invention, the solubility thereof in organic solvents and buffer solutions was studied in comparison with the α-type crystal. The results are shown in Tables 5 to 8.

(1) Test method:

The solubility in organic solvents and buffer solutions (Britton-Robinson Buffer: ionic strength (I)=0.3) was examined.

Specifically, according to the method described in USP 25 (U.S. PHARMACOPEIA 25(USP25), p 8, General Notices, Solubility), crystalline N-(3-chloro-1H-indol-7-yl)-4-sulfamoylbenzenesulfonamide was evaluated in terms of solubility in various organic solvents and Britton-Robinson buffers (pH 3, 5, 7, 9, and 11; I=0.3). The amount of each solvent was recorded that was required to solve a 10-mg sample of (N-(3-chloro-1H-indol-7-yl)-4-sulfamoylbenzenesulfonamide) at 25° C. within 30 minutes. In this study, the container was vigorously shaken for 30 seconds every 5 minutes, and the solubility was visually checked.

(2) Results:

The obtained results are shown in Tables 5 to 8.

TABLE 5

| Solvent | Solvent amount (ml) required to solve 1 g of compound (1) (α-type crystal) |
|---|---|
| Acetone | 21 |
| Ethanol | 1194 |

TABLE 5-continued

| Solvent | Solvent amount (ml) required to solve 1 g of compound (1) (α-type crystal) |
|---|---|
| Acetonitrile | 97 |
| Ethyl acetate | 1090 |
| Heptane | >10000 |
| Isopropylether | >10000 |
| Methanol | 100.4 |
| N,N-dimethylformamide | 9.6 |
| 1-octanol | >10000 |
| Water | >10000 |

TABLE 6

| Solvent | Solvent amount (ml) required to solve 1 g of compound (1) (β-type crystal) |
|---|---|
| Acetone | 14 |
| Ethanol | 373 |
| Acetonitrile | 74 |
| Ethyl acetate | 322 |
| Heptane | >10000 |
| Isopropylether | >10000 |
| Methanol | 60 |
| N,N-dimethylformamide | 6 |
| 1-octanol | >10000 |
| Water | >10000 |

TABLE 7

| Britton-Robinson Buffer (pH) | Solvent amount (ml) required to solve 1 g of compound (1) (α-type crystal) |
|---|---|
| 3 | >10000 |
| 5 | >10000 |
| 7 | >10000 |
| 9 | >10000 |
| 11 | 993 |

TABLE 8

| Britton-Robinson Buffer (pH) | Solvent amount (ml) required to solve 1 g of compound (1) (β-type crystal) |
|---|---|
| 3 | >10000 |
| 5 | >10000 |
| 7 | >10000 |
| 9 | >10000 |
| 11 | 553 |

(2) Results:

As can be understood from the results of Tables 5 to 8, the β-type crystal has higher solubility in the buffer solution (Britton-Robinson Buffer: ionic strength (I(=0.3)) than the α-type crystal.

INDUSTRIAL APPLICABILITY

The present invention enables the obtainment of a novel β-type crystal of N-(3-chloro-1H-indol-7-yl)-4-sulfamoyl-benzenesulfonamide in a single crystal form. The β-type crystal of the present invention has good physical properties such as high solubility in buffer solutions (for example, Britton-Robinson Buffer) and various organic solvents (for example, ethanol, ethyl acetate) in comparison with the α-type crystal, and is suitable for an active ingredient of a pharmaceutical composition used as an antitumor agent, an activated lymphocyte suppressor, or an eating enhancer.

The invention claimed is:

1. A β-type crystal of N-(3-chloro-1H-indol-7-yl)-4-sulfamoylbenzenesulfonamide,
    wherein said β-type crystal has diffraction peaks at a diffraction angle (2θ±0.2°) of 18.4°, 10.2°, 13.3°, 15.4°, 20.0° and 20.4° as measured by powder X-ray diffractometry.

2. A solid pharmaceutical composition containing the crystal set forth in claim 1 as an active ingredient.

3. The β-type crystal according to claim 1, wherein said β-type crystal is obtained by crystallization of N-(3-chloro-1H-indol-7-yl)-4-sulfaxmoylbenzenesulfonamide in the presence of acetonitrile:water (1:1) or isopropanol:water (1:1).

4. The β-type crystal according to claim 1, wherein said β-type crystal is more soluble in organic solvents than an α-type crystal of N-(3-chloro-1H-indol-7-yl)-4-sulfamoyl-benzenesulfonamide, and wherein said organic solvents are selected from the group consisting of: acetone, ethanol, acetonitrile, ethyl acetate, methanol, N,N-dimethylformamide and mixtures thereof.

5. A method of preparing a β-type crystal of N-(3-chloro-1H-indol-7-yl)-4-sulfamoylbenzenesulfonamide according to claim 1, wherein said method comprises:
    crystallizing N-(3-chloro-1H-indol-7-yl)-4-sulfamoyl-benzenesulfonamide in acetonitrile:water (1:1) or isopropanol:water (1:1), thereby producing a β-type crystal of N-(3-chloro-1H-indol-7-yl)-4-sulfamoylbenzene-sulfonamide.

6. A method of improving the solubility of crystal N-(3-chloro-1H-indol-7-yl)-4-sulfamoylbenzenesulfonamide, wherein said method comprises:
    crystallizing N-(3-chloro-1H-indol-7-yl)-4-sulfamoyl-benzenesulfonamide in acetonitrile:water (1:1) or isopropanol:water (1:1),
    thereby improving the solubility of the β-type crystal of N-(3-chloro-1H-indol-7-yl)-4-sulfamoylbenzene-sulfonamide having diffraction peaks at a diffraction angle (2θ±0.2°) of 10.2°, 13.3°, 15.4°, 18.4°, 20.0°, and 20.4° as measured by powder X-ray diffractometry.

* * * * *